(12) United States Patent
Amagase

(10) Patent No.: US 8,613,960 B2
(45) Date of Patent: Dec. 24, 2013

(54) FORMULATIONS AND METHODS FOR REDUCING WAIST CIRCUMFERENCE

(76) Inventor: Harunobu Amagase, Phoenix, AZ (US)

( * ) Notice: Subject to any disclaimer, the term of this patent is extended or adjusted under 35 U.S.C. 154(b) by 0 days.

(21) Appl. No.: 13/114,197

(22) Filed: May 24, 2011

(65) Prior Publication Data

US 2011/0224165 A1 Sep. 15, 2011

Related U.S. Application Data

(63) Continuation-in-part of application No. 12/864,626, filed as application No. PCT/US2009/031992 on Jan. 26, 2009, now abandoned.

(60) Provisional application No. 61/024,831, filed on Jan. 30, 2008.

(51) Int. Cl.
*A61K 36/00* (2006.01)
*A61K 36/815* (2006.01)
*A61K 31/715* (2006.01)

(52) U.S. Cl.
USPC .............................................. 424/725; 514/54

(58) Field of Classification Search
None
See application file for complete search history.

(56) References Cited

U.S. PATENT DOCUMENTS

2005/0064049 A1* 3/2005 Mori et al. ................... 424/725

OTHER PUBLICATIONS

Zhang et al, Isolation of *Lycium barbarum* polysaccharide and its defatting effects on monosodium glutamate induced obesity in female mice, Shipin Kexue (Beijing, China) (2003), 24(3), 114-117.*

* cited by examiner

*Primary Examiner* — Qiuwen Mi
(74) *Attorney, Agent, or Firm* — Quarles & Brady LLP

(57) ABSTRACT

Methods for reducing abdominal fat and waist circumference in a human subject are disclosed. The method includes a composition containing *Lycium* plant that, when administered to a human, can reduce that human's waist circumference.

3 Claims, 5 Drawing Sheets

FORMULATIONS AND METHODS FOR REDUCING WAIST CIRCUMFERENCE

CROSS-REFERENCE TO RELATED APPLICATIONS

This application is a continuation-in-part application of U.S. patent application Ser. No. 12/864,626 (now abandoned), which is National Stage Entry of PCT/US09/31992, filed Jan. 26, 2009, which claims the benefit of U.S. Provisional Patent Application No. 61/024,831, filed Jan. 30, 2008, each of which is incorporated herein by reference as if set forth in its entirety.

FIELD OF THE INVENTION

The invention relates generally to formulations and methods for reducing abdominal fat and waist circumference in human subjects.

BACKGROUND OF THE INVENTION

Obesity is a global health problem that is associated with increased morbidity and mortality (Pi-Sunyer et al., Arch Intern Med 158 (17):1855-1867, (1998); Pischon et al., N Engl J Med 359(20):2105-2120, (2008), incorporated herein by reference as if set forth in their entirety). Abdominal obesity is strongly associated with increased cardiometabolic risk, cardiovascular events, strokes, metabolic syndrome, and mortality (Pischon et al., supra; National heart lung and blood institute, de Koning et al., Eur Heart J 28(7):850-856, (2007) incorporated herein by reference as if set forth in their entirety). Metabolic syndrome is a group of risk factors related to obesity that occur together causing increased risk for coronary artery disease, stroke, and type 2 diabetes. One criterion for diagnosing metabolic syndrome is measurement of abdominal obesity/waist circumference, because visceral adipose tissue is a key component of the syndrome (de Koning et al., supra; American Heart Association, International Diabetes Foundation worldwide definition of the metabolic syndrome, incorporated herein by reference as if set forth in their entirety). Recent research suggests that doctors should prioritize waist circumference rather than body-mass-index (BMI) when assessing a patient's risk of heart disease (Pischon et al., supra; National Heart Lung and Blood Institute, supra; de Koning et al., supra; American Heart Association, supra; International Diabetes Federation, supra). A woman's health is at risk when her waist circumference measures more than 31 inches; a man's health is at risk when his waist circumference is more than 37 inches. Waist circumference measurements greater than 35 inches for women and 40 inches for men are signs of metabolic syndrome.

Methods for reducing abdominal fat include surgery. However, surgery for "spot reducing," such as liposuction, is not an effective long-term solution to reduce waist circumference or disease risk. For example, liposuction removes fat from specific areas of the body (e.g., abdomen, thighs, buttocks), but does not remove fat from organs where it is most dangerous. As an alternative to surgery, many doctors and nutritionists advise their patients to eat less, to avoid calorie-dense foods that are high in fat and/or sugar, and to increase intake of foods such as fruits, vegetables and whole grains, which are filling but not fattening. Additionally, or alternatively, many doctors advise that physical activity should also be incorporated into daily life to reduce weight and abdominal fat.

While many people are aware of dietary and exercise regimens to reduce abdominal fat, such lifestyle changes are difficult, which can impede an individual's ability to successfully implement one or more lifestyle changes. Accordingly, the number of obese individuals is rising. Thus, there is a need in the art for compositions and methods of reducing abdominal fat in individuals that avoid invasive intervention and difficult lifestyle changes.

SUMMARY OF THE INVENTION

The present invention is broadly summarized as relating to a composition containing *Lycium* plant that, when administered to individuals, can reduce that individual's waist circumference. Many methods for reducing waist circumference rely on dietary and exercise regimens with varying degrees of complexity and difficulty. In contrast, the present invention relies on administering to an individual, a composition including *Lycium* extract.

In a first aspect, the invention is summarized as a method of reducing waist circumference in a subject by administering to the subject *Lycium barbarum* plant extract composition.

In one embodiment of the first aspect, the *L. barbarum* extract comprises fruit extract. The fruit of *L. barbarum* is also known as goji and the extract of *L. barbarum* fruit can be referred to as goji juice. Although any concentrations can be utilized for this invention, in a preferred embodiment the fruit extract as a percentage of fresh plant material is about 35%. In another preferred embodiment, although any amounts can be utilized for this invention, the fruit extract comprises a content of *Lycium barbarum* polysaccharides (LBP) equivalent to that found in about 15 to 150 g of fresh *Lycium* fruit, but the invention is not limited to this amount.

In a particular embodiment of the first aspect, about 120 ml of the composition is ingested daily by a human subject, but the invention is not limited to this amount.

In a second aspect, the invention encompasses the use of *Lycium* plants or *Lycium* plant preparations, for the manufacture of food formulations to reduce reducing abdominal fat and waist circumference in a subject ingesting the food formulation.

In a preferred embodiment of the second aspect, *Lycium* plants or *Lycium* plant preparations are packaged for use in the reduction of waist circumference.

These and other features, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

DESCRIPTION OF EXEMPLARY EMBODIMENTS

Figure 1:
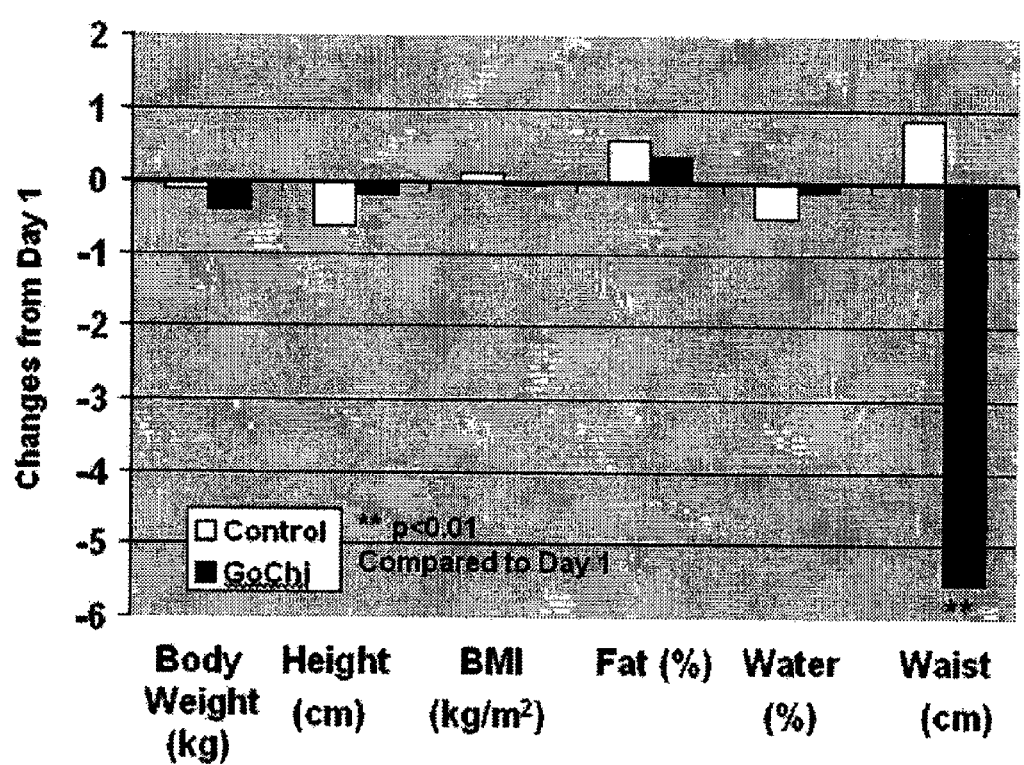
FIG. 1 illustrates changes of parametric markers on day 15 following 14 days of *L. barbarum* treatment.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

In describing the embodiments and claiming the invention, the following terminology is used in accordance with the definitions set out below.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

As used herein, "about" means within 5% of a stated concentration range or within 5% of a stated time frame.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Herein, the inventors provide formulations and methods for reducing abdominal fat and reducing waist circumference in human subjects.

Lycium barbarum (L. barbarum) is a solanaceous defoliated shrubbery and the fruit (goji) has been a commonly prescribed traditional medicine in Asian countries for over 2,500 years. Modern studies indicate that L. barbarum and its main active constituents, L. barbarum polysaccharides (LBP) possess a range of biological effects, such as significantly increasing metabolic rate and body weight reduction in mice and rats. Also observed effects include significant clinical improvements in general well-being, including energy levels, sleep quality, glucose control in diabetics, glaucoma, antioxidant properties, anti-aging, neuroprotection, anti-fatigue/endurance, immunomodulation, anti-tumor activity and cytoprotection.

The Lycium plants in this invention are the plants belonging to the family of solanaceous defoliated shrubbery, such as, for example, Lycium barbarum and Lycium chinense. The most suitable plant for this invention is Lycium barbarum (known as goji, gouqizi, Fructus lycii, or wolfberry). The preferred portion for this invention is the fruit of this plant. Leaf, root or stem may also be utilized for this invention. These materials can be processed as juice or dried by processing and/or extraction methods commonly known in the art.

In addition, the materials derived from the cell culture of the plants can also be utilized as materials for this invention. The juice or extract of the Lycium plants in this invention is preferably the preparation made from plant materials prepared or extracted from water or alcohol. The Lycium plants for the preparation or extraction can be squeezed or crushed with or without a moderate temperature to effect extraction efficiency, as is routinely understood in the art. It is also possible to crush and homogenize the plants to make the juice after separating skin, seeds and other parts. The extract prepared for dietary intake can be utilized as is, in concentrated fluid or powder form after concentration under vacuum or lyophilization.

The administrative dosage of the preparation effective to reduce reducing abdominal fat and waist circumference is varied by the age, body weight or body condition of the human subject. It is recommended to take orally 0.1 oz (3 ml) through 33 oz (990 ml) in a day by adults as a liquid preparation of Lycium plants or extracted Lycium plants. The more feasible and preferred dosage ranges approximately from 1 oz (30 ml) to 8 oz (240 ml) of the preparations per day for an adult human.

The following examples describing materials and methodology are offered for illustrative purposes only, and are not intended to limit the scope of the present invention.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference.

It is understood that the invention is not confined to the specific reagents, formulations, reaction conditions, etc., herein illustrated and described, but embraces such modified forms thereof as come within the scope of the following claims.

The invention will be more fully understood upon consideration of the following non-limiting Examples.

EXAMPLES

Example 1

The Effect of Orally Consumed Lycium Fruit Juice on Waist Circumference

This example describes a controlled study which examined the effects of orally consumed goji berry juice (GoChi) on waist circumference. Lycium barbarum (L. barbarum) is a Solanaceous defoliated shrubbery whose fruit (goji) has been prescribed in traditional medicine in Asian countries for over 2,500 years as a means to improve vision, kidney and liver function, and for its anti-aging benefits (Amagase & Farnsworth, Food Res Int. 10.1016/j.foodres.2011.03.027 (2011); Chang & But, Gouqizi. In Chinese Materia Medica: Chemistry, Pharmacology and Applications 2:852-854 (2001); Zhu, Gou Qi Zi. In Chinese Materia Medica: Chemistry, Pharmacology and Applications pp. 642-646 (1998); Bensky & Gamble, Gou Qi Zi. In Chinese Materia Medica: Chemistry, Pharmacology and Applications pp. 333-334 (1993); Bryan et al. Goji (*Lycium* spp) In Natural Standard Monograph. *Natural Standard Inc.* (2008); incorporated herein by reference as if set forth in its entirety). Modern studies indicate that *L. barbarum* and its main active constituents, *L. barbarum* polysaccharides (LBP), possess a range of biological effects, such as increasing metabolic rate and reducing body weight in mice and rats (Zhang et al., J Hygiene Res 31(2):118-9, 2002; Nance et al., Brain Behav Imm 23(Suppl 2):S51, (2009); incorporated herein by reference as if set forth in its entirety). Other effects associated with consuming *L. barbarum* include clinical improvements in energy levels, sleep quality, glaucoma, glucose control in diabetics, anti-oxidant properties, anti-aging, neuroprotection, anti-fatigue/endurance, immunomodulation, anti-tumor activity and cytoprotection (Gou, "Chinese Herbal Medicine, Materia Medica" pp. 333-334 (1993); Gouqizi. "Pharmacology and Applications of Chinese Materia Medica" Vol. 2. pp. 852-4 (2001); Amagase et al., J Alt Comp Med 14:403-412 (2008); Amagase et al., FASEB J 23:716.1 (2009); Amagase et al., J Med Foods 12 (5): 1159-1165 (2009); Amagase et al., Nutr Res 29:19-25 (2009); Chang et al., Cell Mol Neurobiol 28 (5):643-652 (2008); incorporated herein by reference as if set forth in their entirety). *Lycium barbarum* is also referred to as goji, gouqizi, *Fructus lycii*, or wolfberry.

Materials And Methods

A controlled study was designed and carried out to determine the efficacy of orally consumed goji berry, *L. barbarum*, as a standardized juice (GoChi) as a means to reduce waist circumference in healthy adults. Healthy adult subjects consumed 120 ml (4 oz) of GoChi or a placebo control daily for 14 days. All subjects performed 15 minutes walking as exercise and all subjects ingested no food or snack after 7 pm during the test period. GoChi or the placebo control was consumed twice daily: 90 ml (3 oz) in the morning and 30 ml (1 oz) right before bed time. Data were statistically analyzed for changes between day 1 and day 15.

Results

Figure 2:
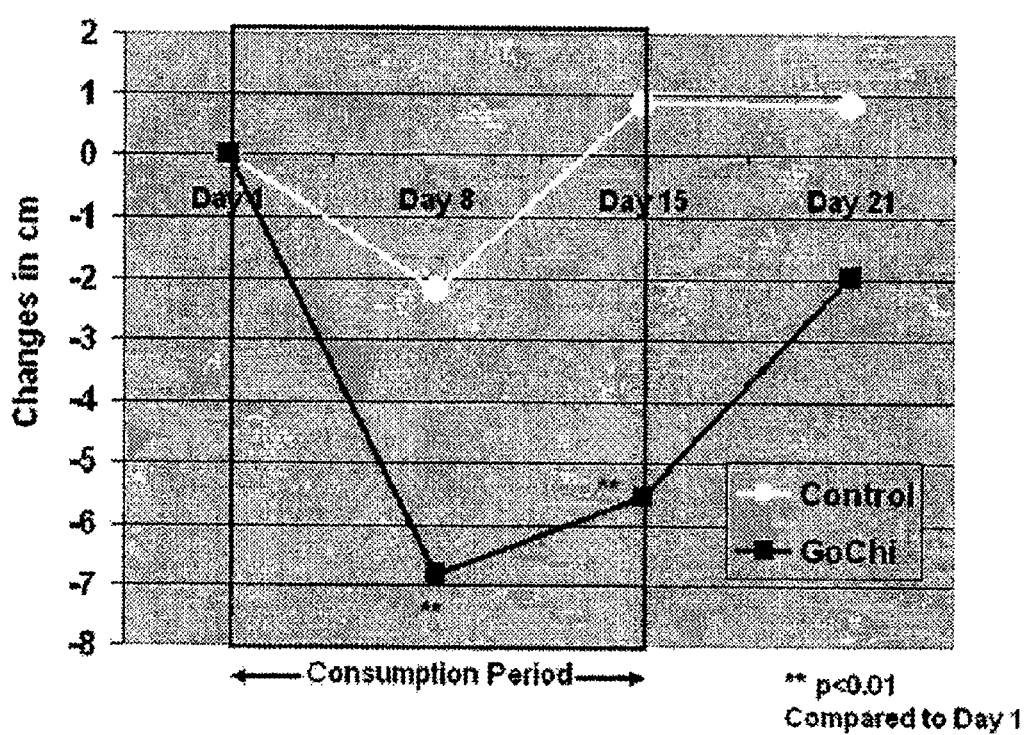
FIG. 2 illustrates changes in waist circumference measured during and following 14 days of *L. barbarum* treatment.

Waist circumference in the GoChi group (N=14) on day 15 was reduced by 5.54 cm from day 1 (p<0.01). All other parametric data (body weight, etc.) were not significantly different between control and GoChi groups or between day 1 and day 15 for either group. In contrast, the placebo group (N=14) showed no significant change in any parameter, including waist circumference (FIG. 1). The reduction in waist circumference in the GoChi group was evident within 8 days of GoChi intake and waist circumference reduction was maintained throughout the 14-day GoChi treatment (FIG. 2). Taken together, these results clearly indicate that daily consumption of GoChi for 14 days reduces waist circumference.

Example 2

*Lycium Barbarum* Increases Caloric Expenditure and Decreases Waist Circumference in Overweight Men and Women Based on the known features of *L. barbarum*, two human clinical studies were conducted to explore the acute effects of *L. barbarum* on 1) resting metabolic rate (RMR) and postprandial energy expenditure (PPEE) measured by indirect calorimetry, and 2) central adiposity as measured by waist circumference in healthy human subjects using a *L. barbarum* fruit juice, GoChi®, which is standardized with regards to its active component, LBP. A single bolus of *L. barbarum* intake increased postprandial energy expenditure (PPEE) 1 through 4 h post-intake over the baseline level in a dose-dependent manner. In a 14-day intervention trial, individuals consuming *L. barbarum* exhibited significantly decreased waist circumference. These results show that *L. barbarum* consumption increases metabolic rate and reduces waist circumference in humans relative to placebo-treated control subjects.

Materials And Methods

*L. barbarum* and Placebo Preparation:

FreeLife International Inc. (Phoenix, Ariz.) supplied a commercially available, LBP-standardized *L. barbarum* fruit juice (GoChi; Lot No. ASA07120 and ASA07351) produced from fresh ripe *L. barbarum* fruit. The yield of juice as a percentage weight of the starting fresh plant material was about 35%. Juice was processed in an aseptic manner at an industrial scale and kept refrigerated at 2 to 8° C. Description and standardization procedures of the test material were previously described (Amagase et al., Alt Comp Med 14:403-412 (2008), incorporated herein by reference as if set forth in its entirety). Briefly, *L. barbarum* fruit juice was standardized to contain a content of LBP equivalent to that found in at least 150 g of fresh fruit per daily intake (120 ml), the amount customarily consumed in Traditional Chinese Medicine to elicit anti-aging effects and to stimulate metabolism (Yu et al., Int J Mol Med 20 (2):261-268 (2007), incorporated herein by reference as if set forth in its entirety). Caloric amount of 120 ml of *L. barbarum* preparation was 64 kcal.

The placebo control material (Lot No. A198), supplied by FreeLife International, matched the color, flavor, and taste of *L. barbarum* fruit juice in a formulation of sucralose (10 mg), artificial fruit flavor (30 mg), citric acid (60 mg), and caramel color (12 mg) in 30 ml of purified water. The placebo was packaged in the same type of container as the *L. barbarium* fruit juice; the placebo contained no LBP.

Study Population:

Participants were healthy men and women 18 years and older who were recruited separately for each study. In all clinical studies, the same inclusion/exclusion criteria to select subjects were used, but separate protocols were provided for each study. Subjects were excluded from the studies if they exhibited any evidence of heart, liver, lung, or kidney disease; had known allergies to *L. barbarum* or other fruit juices; were pregnant or breast feeding; were under anticoagulant therapy such as Coumadin® (warfarin); or had any acute or chronic medical or psychiatric conditions. All subjects were fully informed of the purpose of the study, and signed the Human Subjects Informed Consent forms approved by the Internal Review Board organized under the Helsinki Declaration. Based on the background information provided by the subjects, study groups did not differ in pre-study dietary intake, average *L. barbarum* consumption history, consumption patterns for other beverages, such as sweetened beverages (soda), coffee, tea and alcoholic beverages, or smoking habits.

Research Protocol:

Two separate clinical studies were conducted in a randomized, double-blind, placebo-controlled manner. Following enrollment in the trial, all participants completed at least two weeks of a wash-out period during which time they were to discontinue their use of any *L. barbarum* or *L. barbarum*-containing foods, any dietary supplements, energy drinks, caffeinated beverages, or green tea. These restrictions were continued throughout the study based upon self-declaration in the daily dietary diary and verbal confirmation.

Figure 3:
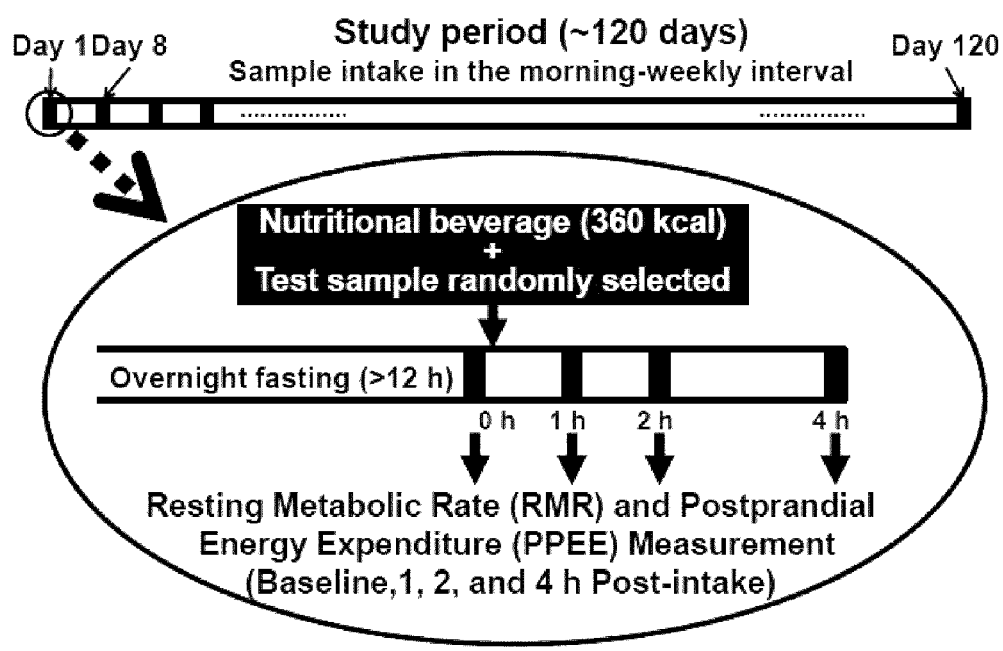
FIG. 3 illustrates the testing procedure for resting metabolic rate (RMR) and postprandial energy expenditure (PPEE).

Resting Metabolic Rate (RMR) and Postprandial Energy Expenditure (PPEE) Measurement:

Energy expenditure/caloric metabolism activity indicated by RMR and PPEE was measured by breath oxygen volume ($VO_2$ ml/min) using a hand-held indirect calorimeter (MedGem® test kit, Health Tech, Inc., Golden, Colo.). Testing conditions were standardized across all subjects and followed previously established recommendations (St-Onge et al., Obes Res. 12:704-709 (2004), incorporated herein by reference as if set forth in its entirety). RMR and PPEE were measured for 10-15 minutes following at least 15 minutes resting. A total of 8 subjects (21-51 y, age=34.5±7 y, body mass index (BMI)=28.2±2 kg/m$^2$) were enrolled in and completed a randomized, double-blind, placebo-controlled, multiple-period crossover study. All test subjects randomly consumed 1 test sample preparation per test day. They repeated the same sample in a duplicate measurement on a different day. Test days were at least 1 week apart from the previous sample intake. On a test day prior to treatment, basal metabolic rate was measured following least a 12 h overnight fast. Subjects then consumed a nutritional beverage (360 kcal, Boost Plus®, Nestle Healthcare Nutrition Inc., Minneapolis, Minn.) with known caloric content as breakfast to stabilize RMR throughout the 4 h testing period. In addition to the nutritional beverage, a single bolus containing 120 ml of one of 3 doses of *L. barbarum* (30, 60, and 120 ml) or a placebo sample bolus was given to each subject. Total consumption volume of the test sample was 120 ml each time; 90 or 30 ml of placebo solution was added to 30 or 60 ml of *L. barbarum* sample solution, respectively to make up a final volume of 120 ml. RMR was measured immediately before (baseline) treatment, 1, 2, and 4 h post treatment (FIG. 3). RMR and PPEE were measured by breath oxygen volume ($VO_2$ ml/min) using a hand-held indirect calorimeter in a randomized, double-blind, placebo-controlled, multiple-period crossover study. All test subjects consumed 1 of 8 separate test samples that were presented randomly to subjects at weekly intervals, and each sample was tested twice. Study period was up to 120 days.

Waist Circumference and Morphometric Measurements:

A randomized, placebo-controlled, double-blind clinical study was performed in a 14-day intervention period to evaluate the effect of *L. barbarum*, relative to placebo (120 ml/d), on waist circumference and other morphometric parameters. Subjects were randomly assigned to either the *L. barbarum* treatment group or the placebo control group. Physical morphometric measurements were taken at the pre-, middle-, and post-intervention period following an overnight, 12 h fast and included: body weight, BMI (Seca® 703, Hamburg, Germany), waist circumference at the level of umbilicus, and total body fat (Tanita® BF-679W, Tokyo, Japan). All participants were monitored daily to ensure full compliance with the protocol, including sample consumption and restriction of dietary intake. Compliance was confirmed by the daily consumption of the samples in front of a research coordinator and also checked by returned empty sample bottles everyday during the weekdays, and the following Monday after the weekend. Individuals administering the physical exams were blinded as to the treatment conditions, and the treatment codes were not broken until the study was completed. *L. barbarum* or placebo sample consumption was combined with a diet restriction and exercise program in overweight/obese subjects with BMI>25 kg/m$^2$ (25.6-45.3, average BMI=29.3±1.1 kg/m$^2$). Based upon our previous studies [Amagase et al., J Alt Comp Med 14:403-412 (2008); Amagase et al., FASEB J 23:716.1 (2009); Amagase et al., J Med Foods 12 (5): 1159-1165 (2009); Amagase et al., Nutr Res 29:19-25 (2009); incorporated herein by reference as if set forth in their entirety), a sample size of 35 subjects was deemed sufficient to detect effectiveness of *L. barbarum* with 95% confidence and 80% power. A total of 33 healthy adults (19-60 years, average age 33.6±1.9 y) consumed 90 ml of *L. barbarum* or placebo each morning with a meal and 30 ml at bedtime for 14 days. Daily 15 minute-walks (after lunch during weekdays) were implemented for all subjects. Subjects wore study-provided pedometers and daily steps were recorded in a log. Caloric intake per day was restricted to approximately 1,200 kcal during the 14-day treatment; caloric intake was monitored using daily dietary diaries maintained by the subjects. Sixty-seven percent of study subjects were women. Four dropouts (2 in each group) occurred due to personal issues unrelated to the sample or study.

Statistical Analysis:

Dietary intake data were analyzed with the non-parametric Mann-Whitney U-Test (placebo vs *L. barbarum*). All parametric data (body weight, height, BMI, waist circumference, body fat lean mass, $VO_2$ and RMR) were analyzed by ANOVA for independent and dependent groups. Descriptive statistics were calculated for placebo and *L. barbarum* for all dependent measures and summarized as means and standard errors. The data were processed using Statistica® version 8 (StatSoft®, Inc., Tulsa, Okla.). Differences were considered significant at $p<0.05$.

Results

Figure 4:
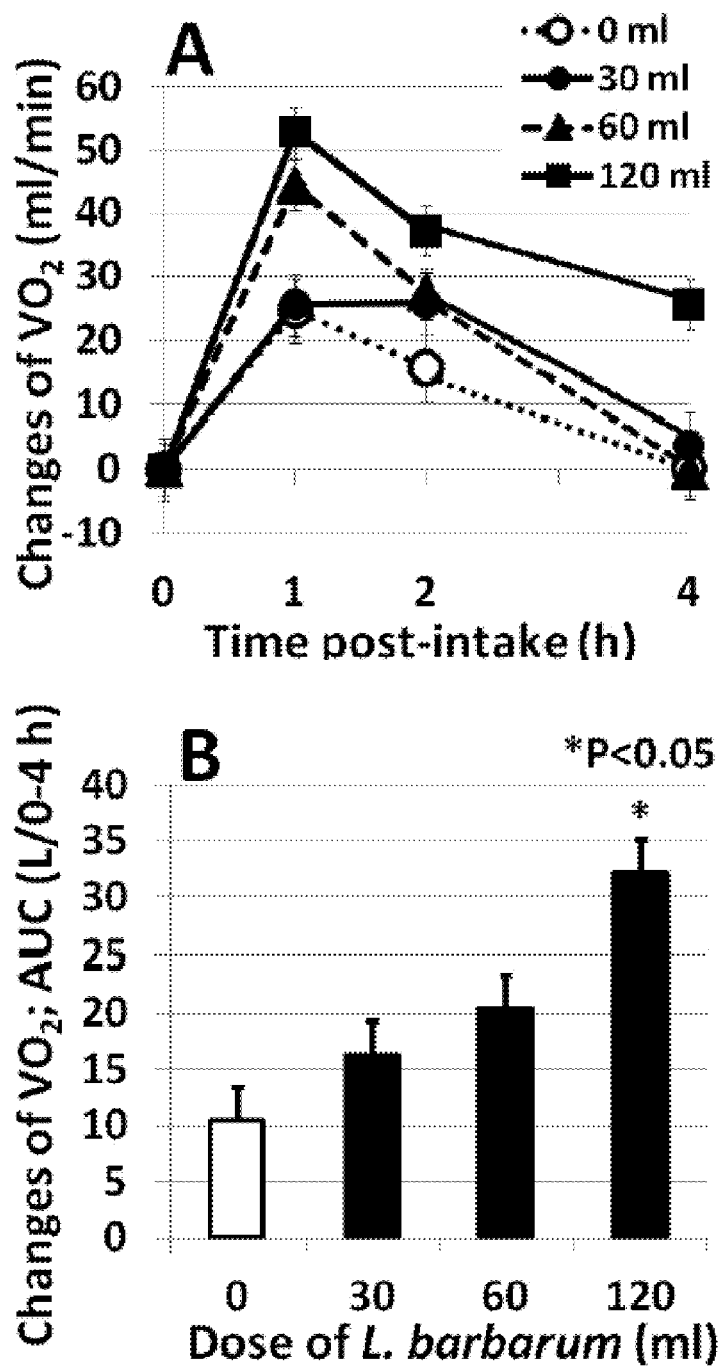
FIG. 4 illustrates the dose-response relationship of *L. barbarum* on (A) kinetic changes and (B) area under the curve (AUC) of the breath oxygen level ($VO_2$) analyzed by indirect calorimetry during four hours after treatment. Each value indicates mean±SEM.* indicates significant increase from control level ($p<0.05$).

Resting Metabolic Rate (RMR) and Postprandial Energy Expenditure (PPEE):

The average baseline level of $VO_2$ in all subjects was 253.58±13.13 ml/min which was equivalent to 1,761.04±27.17 kcal/day. The placebo and all single boluses of various dosages of *L. barbarum* intake with nutritional beverage (360 kcal) increased RMR calculated from $VO_2$ measurement over the baseline level. At 1 h post-intake, 120 ml of *L. barbarum* intake increased 58.26±5.72 ml/min of $VO_2$ over the baseline level and was significantly higher than the placebo group (24.58±4.04 ml/min) ($p<0.05$) (FIG. 4A). At 4 h post-intake, placebo control and all doses of *L. barbarum* except 120 ml intake returned to the baseline level. Conversely, $VO_2$ level after 120 ml of *L. barbarum* intake was maintained at a significantly higher level than other doses of *L. barbarum* or placebo control group ($p<0.05$) (FIG. 4A).

The area under the curve (AUC) of $VO_2$ during 0 to 4 h post-intake of placebo control sample was 10.42±4.09 L in 4 h. The AUC of $VO_2$ after 120 ml of *L. barbarum* intake was significantly increased by 32.19±3.01 L in 4 h which was more than twice that of the placebo level ($p<0.05$) (FIG. 3B). The stimulus effect of *L. barbarum* on metabolic rate/energy expenditure occurred in a dose-dependent manner (FIGS. 4A and 4B).

Figure 5:
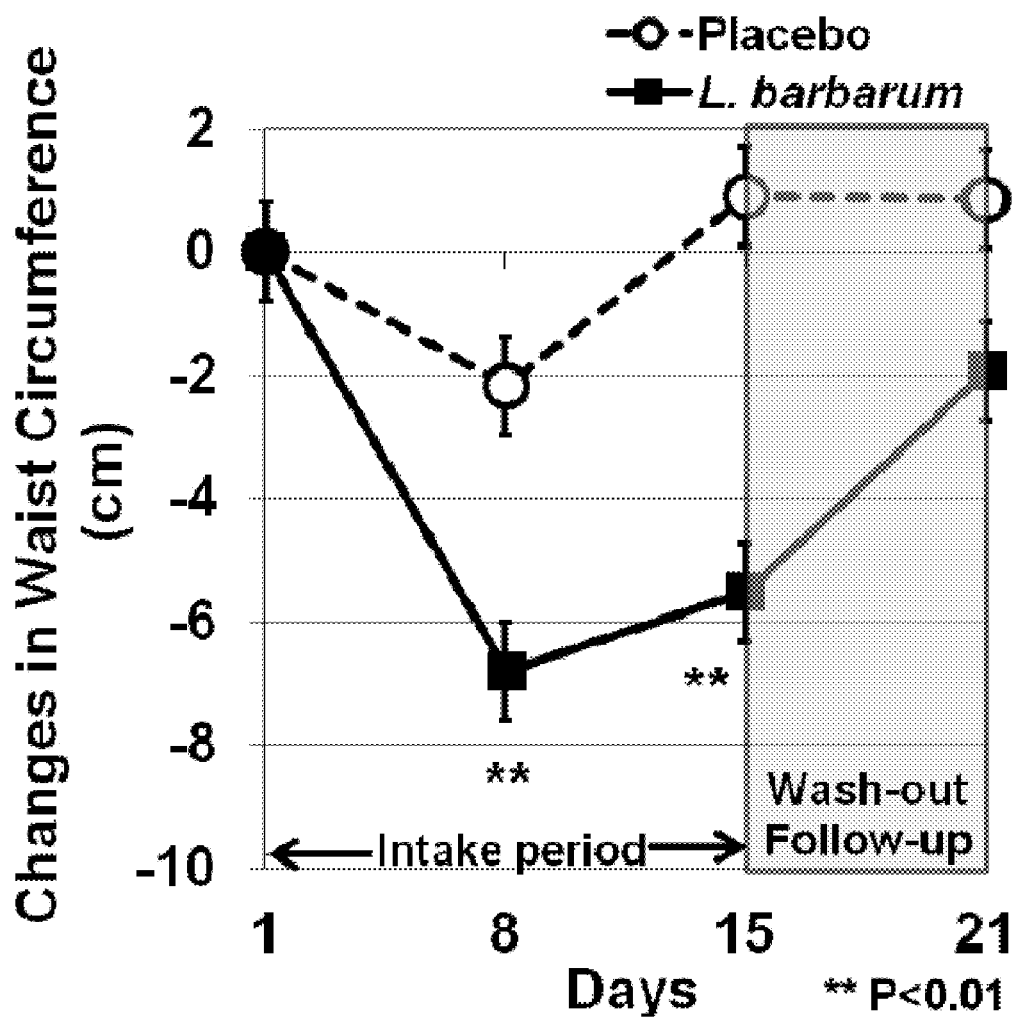
FIG. 5 illustrate changes of the waist circumference in human subjects during and after the 14-day intervention period. Each value indicates mean in cm±SEM. ** indicates significant difference from the pre-intervention level and the placebo group ($p<0.01$).

Waist Circumference:

In the 14-day treatment study, daily intake of *L. barbarum* combined with exercise and dietary restriction decreased waist circumference significantly in both middle- and post-treatment ($p<0.01$) (FIG. 5). Reduction in waist circumference in the *L. barbarum* group (n=14) at post-treatment on Day 15 was 5.54±0.65 cm relative to pre-treatment (FIG. 5). In the placebo group (N=15), the change in waist circumference on Day 15 relative to pre-treatment was only 0.88±0.83 cm; this change is insignificant.

Other morphometric parameters, such as body weight, BMI and total body fat did not show any statistically significant differences from the pre-treatment measurements in either group. Average change in body weight on Day 15 in the *L. barbarum* group compared to pre-treatment was −0.40±0.37 kg; average change in body weight on Day 15 in the placebo group compared to pre-treatment was −0.10±0.17 kg. Thus, *L. barbarum*, in combination with modest exercise and diet restriction has a significant effect on waist circumference.

Discussion

Results of these studies suggest that *L. barbarum* increased energy expenditure in human subjects. Consumption of *L. barbarum* can lead to a reduction in central adiposity, as indicated by the reduction in waist circumference exhibited by subjects when combined with moderate dietary caloric intake restriction and mild exercise. The active compound of *L. barbarum*, LBP, reportedly enhances food conversion rate in murines and reduces murine body weight following 10-21 days of consumption (Zhang et al., supra; Nance et al., supra). These results suggest that *L. barbarum* can modulate metabolism in vivo and may correspond with the present study's result regarding the effects of *L. barbarum* on RMR/PPEE and waist circumference. These metabolic effects may also be related to the changes in adrenocortical hormone levels which contribute to energy regulation and obesity control. The randomized, double-blind, placebo-controlled human study presented herein with five male subjects has shown that a single bolus intake of *L. barbarum* (120 ml) significantly reduced fasting salivary levels of cortisol and dehydroepiandrosterone at 7 am by 46% and 27%, respectively compared with the placebo control group ($p<0.05$). Cortisol reportedly increases obesity and metabolic syndrome. Thus, reduction of cortisol by *L. barbarum* might contribute to increased metabolic rate and decreased waist circumference.

Metabolic rate/energy expenditure was acutely and significantly increased by *L. barbarum* treatment compared to placebo treatment, and this effect may be dose-dependent. In vivo enhancement of metabolic rate by *L. barbarum* intake may contribute to changes in waist circumference and waist-related parameters observed in the present studies. The lack of change in body weight may reflect insufficient duration of exposure to *L. barbarum* and its bioactive compounds, since the present studies were short term trials. Alternatively, *L. barbarum* effects might be specific to the central adiposity and independent from weight loss, such is the case with capsinoid treatment (Snitker et al., Am J Clin Nutr 89:45-50 (2009), incorporated herein by reference as if set forth in its entirety). Capsinoid can significantly reduce abdominal fat in an individual without significantly reducing that individual's body weight. Oral administration of LBP reduced serum total cholesterol, LDL and triglyceride concentrations and increased high density lipoprotein levels in rabbits and mice. However, detailed analysis of the effect of *L. barbarum* on fatty acid metabolism in vivo was not performed in the present studies. Central adiposity analysis by Dual-emission X-ray absorptiometry (DXA) and lipid metabolism profile tests are required to determine the detailed effect of *L. barbarum* on fat metabolism including the specific location of effected fat tissues in the body.

The experiments described herein above are the first randomized clinical trials to evaluate the role of *L. barbarum* on metabolic parameters in humans. Results suggest that daily consumption of *L. barbarum* in the form of fruit juice (Go-Chi) stimulates metabolic rate and reduces in waist circumference.

It is understood that certain adaptations of the invention described in this disclosure are a matter of routine optimization for those skilled in the art, and can be implemented without departing from the spirit of the invention, or the scope of the appended claims. All publications and patents mentioned in the above specification are herein incorporated by reference. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come with the scope of the following claims.

The invention claimed is:

1. A method of reducing waist circumference in a human subject, comprising orally administering to the subject *Lycium barbarum* plant extract composition wherein about 120 ml of the composition comprising a content of *Lycium barbarum* polysaccharides equivalent to that found in about 150 g of fresh *Lycium* fruit is ingested daily.

2. The method of claim 1, wherein the *Lycium barbarum* extract comprises fruit extract.

3. The method of claim 2, wherein the fruit extract as a percentage of fresh plant material is about 35%.

\* \* \* \* \*